United States Patent
Möhler et al.

(10) Patent No.: US 9,377,405 B2
(45) Date of Patent: Jun. 28, 2016

(54) EVALUATION CIRCUIT FOR AN OPTOELECTRONIC DETECTOR AND METHOD FOR RECORDING FLUORESCENCE EVENTS

(71) Applicant: Carl Zeiss Microscopy GmbH, Jena (DE)

(72) Inventors: Gunter Möhler, Jena (DE); Dietmar Schmidt, Bibra (DE); Oliver Holub, Jena (DE); Robert Hauschild, Wein (AT)

(73) Assignee: Carl Zeiss Microscopy GmbH, Jena (DE)

(*) Notice: Subject to any disclaimer, the term of this patent is extended or adjusted under 35 U.S.C. 154(b) by 37 days.

(21) Appl. No.: 14/348,261

(22) PCT Filed: Sep. 20, 2012

(86) PCT No.: PCT/EP2012/003939
§ 371 (c)(1),
(2) Date: Mar. 28, 2014

(87) PCT Pub. No.: WO2013/045053
PCT Pub. Date: Apr. 4, 2013

(65) Prior Publication Data
US 2014/0231675 A1      Aug. 21, 2014

(30) Foreign Application Priority Data

Sep. 30, 2011 (DE) .................. 10 2011 114 874

(51) Int. Cl.
*G01J 1/58* (2006.01)
*G01N 21/64* (2006.01)
*G01J 3/28* (2006.01)
*G02B 21/00* (2006.01)
*G01J 1/44* (2006.01)
*G01J 3/44* (2006.01)

(52) U.S. Cl.
CPC . *G01N 21/64* (2013.01); *G01J 1/44* (2013.01); *G01J 3/2889* (2013.01); *G01J 3/44* (2013.01);
(Continued)

(58) Field of Classification Search
CPC .............. G01N 21/64; G01N 21/6408; G01N 21/6458; G01J 1/44; G01J 3/2889; G01J 3/44; G02B 21/0076; G02B 21/0084
USPC ...................................... 250/459.1
See application file for complete search history.

(56) References Cited

U.S. PATENT DOCUMENTS 3,439,342 A * 4/1969 Barton
4,794,464 A * 12/1988 Sasson .......................... 386/308
(Continued)

FOREIGN PATENT DOCUMENTS

| DE | 26 04 460 | 8/1977 |
|---|---|---|
| DE | 10 2008 029458 | 12/2009 |
| WO | WO 01/63223 | 8/2001 |

OTHER PUBLICATIONS

English translation of the International Preliminary Report on Patentability for PCT/EP2012/003939 dated Apr. 1, 2014.
(Continued)

*Primary Examiner* — David Porta
*Assistant Examiner* — Edwin Gunberg
(74) *Attorney, Agent, or Firm* — Frommer Lawrence & Haug LLP (57) ABSTRACT

An improved evaluation circuit which allows high sensitivity in an economical manner. For this purpose, a shift register having at least one data input, a clock input, a plurality of register stages and at least one data output is provided, wherein the output of the analog-to-digital converter is connected to the data input of the shift register. With a shift register, fluorescent light and scattered light can be temporally distinguished in an economical manner.

13 Claims, 6 Drawing Sheets

(52) U.S. Cl.
CPC ........ *G01N 21/6408* (2013.01); *G01N 21/6458* (2013.01); *G02B 21/0076* (2013.01); *G02B 21/0084* (2013.01)

(56) References Cited

U.S. PATENT DOCUMENTS

| | | | |
|---|---|---|---|
| 5,283,433 A * | 2/1994 | Tsien | 250/234 |
| 7,307,558 B1 * | 12/2007 | Karim et al. | 341/100 |
| 2001/0015411 A1 | 8/2001 | Ohdaira et al. | |
| 2003/0010116 A1 | 1/2003 | Cavazzin et al. | |
| 2011/0119034 A1 | 5/2011 | Liedtke et al. | |
| 2011/0149290 A1 * | 6/2011 | Schulte et al. | 356/445 |
| 2011/0149388 A1 | 6/2011 | Liedtke et al. | |

OTHER PUBLICATIONS

International Search Report for Application No. PCT/EP2012/003939 dated Mar. 5, 2013.

* cited by examiner

EVALUATION CIRCUIT FOR AN OPTOELECTRONIC DETECTOR AND METHOD FOR RECORDING FLUORESCENCE EVENTS

The present application claims priority from PCT Patent Application No. PCT/EP2012/003939 filed on Sep. 20, 2012, which claims priority from German Patent Application No. DE 10 2011 114 874.8 filed on Sep. 30, 2011, the disclosures of which are incorporated herein by reference in their entirety.

FIELD OF THE INVENTION

The invention is directed to an evaluation circuit for evaluating the electric signals of an optoelectronic detector, particularly during the capture of fluorescence events during excitation by means of light pulses, comprising an analog-to-digital converter (ADC) with an input for connecting to an output of the detector and with an output for outputting a digital value, and to a method for recording fluorescence events by means of an optoelectronic detector, particularly in a microscope, wherein light pulses are radiated onto a sample by means of a light source and light from the sample is captured by means of the detector and is converted into an electric signal and fed to an analog-to-digital converter. The light pulses present a series of illumination cycles.

Within the meaning of the invention, the term "light" includes not only visible (perceptible to the human eye) electromagnetic radiation, but any electromagnetic radiation that can be manipulated by optical means (particularly refraction, diffraction, polarization and dispersion), i.e., for example, infrared radiation and ultraviolet radiation.

Scattered light in any form is undesirable for high-sensitivity fluorescence measurement regardless of whether it is direct excitation light arriving in the detection channel (in spite of spectral separation), diffuse scattered light of optical components, excitation light reflected at surfaces, or light scattered from the sample (particularly Rayleigh scattered light and Raman scattered light). Raman scattering takes place at the solvent contained in the samples to be examined and cannot be prevented in any excited sample. In aqueous biological samples, the scattered light occurring through Raman scattering is typically spectrally located in the wavelength range of the fluorescence emission and presents an obstacle to precise measurements which cannot be overcome by commonly used spectral filtration. Conversely, fluorescence interferes with the measurement of a Raman spectrum which is typically carried out for determining the molecules present in the sample because the fluorescence cannot be spectrally filtered from the Raman spectrum.

It is noted that citation or identification of any document in this application is not an admission that such document is available as prior art to the present invention.

An evaluation circuit for measuring pulse-excited fluorescence with an analog-to-digital converter is known from the prior art, for example, US 2001/0015411 A1. However, the evaluation circuit described therein requires a synchronization of the analog-to-digital converter with the light pulses so that either only fluorescent light can be captured or it is impossible to distinguish between fluorescent light and scattered light, particularly not retrospectively.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

It is the object of the invention to improve an evaluation circuit of the type mentioned above so as to allow a highly sensitive detection in an economical manner.

According to the invention, the evaluation circuit has a shift register with at least one (serial) data input, a clock input, a plurality of register stages and at least one (serial or parallel) data output, wherein the output of the analog-to-digital converter is (indirectly or directly) connected to the data input of the shift register. The shift register can be several bits wide in binary logic, for example, i.e., it can receive one or more bits in parallel in each stage. If the shift register is several bits wide, a plurality of simultaneously detected fluorescence events can be stored in the same register stage. For this purpose, a reference value is advisably defined for the analog-to-digital converter, which reference value corresponds to a temporally coincident detection of a quantity of fluorescence events coinciding with the quantity of quantization levels. The digital value outputted by the ADC is then greater than one.

By means of the invention, the light intensities captured by the detector at different times can be stored independently from one another in the stages of the shift register in the form of the digital values outputted by the analog-to-digital converter (A-D converter). This makes it possible to analyze the detected fluorescence events later in a time-resolved manner without needing to store a time stamp for each event during detection in a time-consuming manner. The storage of each digital value is advisably carried out in the input stage of the shift register, which is generally the first register stage. Storage in the shift register includes applying the digital value to a data input of the shift register (input stage), for example, in the form of electric voltages representing bits, and shifting the contents of the register stages to the next respective stage.

During fluorescence detection, both elastic Rayleigh scattering and Raman scattering of the excitation light can be completely eliminated by the possibility thus afforded of temporal discrimination without time-consuming time stamps and statistical analysis thereof. In addition, in contrast to known types of time-correlated single photon counting (TCSPC), all occurring fluorescence photons registered by the detector are processed.

Embodiment forms in which the contents of the shift register are shifted by one stage at the occurrence of a digital value differing from zero are particularly advantageous. To this end, the output of the analog-to-digital converter is preferably also connected to the clock input of the shift register. In this way, time intervals without a fluorescence event do not take up any storage slots in the shift register. The shifting preferably takes place exclusively at the occurrence of a non-zero digital value.

In possible alternative embodiment forms, the contents of the shift register are shifted by one stage repeatedly after a predefined time, particularly by means of a clock generator. For this purpose, the evaluation circuit preferably comprises a clock generator with a predefined or predefinable clock frequency which is connected to the clock input of the shift register. In this embodiment form, time intervals without fluorescence events are also stored in the shift register. With a constant clock, each register stage corresponds to one of a plurality of time intervals of identical duration. Accordingly, based on the position in the register, i.e., based on the current number of the respective register stage, the times of the individual fluorescence events can be reconstructed retrospectively even without time stamps, which makes it possible to reduce the required transmission bandwidth compared to the prior art. The accuracy of the reconstruction depends exclusively on the clock periods. To reduce the amount of data to be transmitted, intervals in which no events have occurred need to not be transmitted or stored. Alternatively, such intervals can be compressed in order to save bandwidth. For example, instead of N zero values, one zero value and the quantity N can be transmitted or stored.

Preferably, a signal which is synchronized with exciting light pulses (particularly with the start thereof) is identified and, at the expiration of a predefined or predefinable time thereafter, a marking value is stored in the input stage in addition to, or instead of, the digital value. For this purpose, the evaluation circuit can comprise a delay circuit with variably adjustable time delay which has an input for a signal (indicating a light pulse, particularly the start thereof) and an output for outputting the signal after the (presently) selected delay, wherein the output of the delay circuit is connected to the data input of the shift register such that, as a result of outputting the delayed signal, a marking value, particularly a zero value, is presented at the data input in addition to, or instead of, the digital value. The shifting of the contents of the register stages to the next respective stage is then carried out, for example, exclusively upon occurrence of a non-zero digital value and when the delayed signal is outputted. For example, in case of a shift register which is a plurality of bits wick, an individual bit can be reserved in each register stage for the marking value, while the leftover bit or, in case of a total width of three or more bits, the rest of the bits are available for accepting digital values.

The marking value gives the time of the occurrence of the delayed signal fluorescence events located before it or after it in the shift register and accordingly defines two time windows within each illumination cycle. This allows temporal separation of scattered light and fluorescent light because fluorescent light is emitted after a time delay (in the nanosecond range) of the excitation time, whereas scattering processes occur so quickly in time that they can be considered (for all practical purposes) as instantaneous with the excitation time. Depending on the purpose of a measurement, the detected fluorescence intensities (for example, for fluorescence microscopy) as well as the detected scattered light intensities (for example, for Raman spectroscopy or Raman microscopy) can be used for further analysis and imaging. In embodiment forms in which the shift clock is determined by the output of the analog-to-digital converter, the device-dependent inaccuracy in the setting of the delay defines the resolution between scattered light and fluorescent light. The period corresponding to the shift frequency of the shift register can then be appreciably longer than the delay without sacrificing the accuracy of the evaluation circuit. On the other hand, with a constant shift clock, the clock period defines the resolution between scattered light and fluorescent light.

The pulsed light excitation combined with the time-tagged detection allows the temporal separation of fluorescent light signals and scattered light signals in an economical manner. In this way, all of the forms of scattered light mentioned above can be completely suppressed and therefore efficiently separated from fluorescent light which is emitted later in time. Also, the light occurring through Raman scattering is completely suppressed by means of this method. Raman scattered light is suppressed regardless of the solvent used in the sample. This allows highly sensitive studies of fluorescence emissions of very low light intensity (with a very small quantity of fluorescing molecules) which were not possible heretofore due to preponderant Raman scattered light and which were therefore accessible until now only to highly sensitive, purely spectroscopic instruments. Measurements of Raman spectra likewise profit from the methods described herein when only the emitted light which is emitted practically simultaneously with the sample excitation is spectrally analyzed. The temporal separation of the intensity proportions can be regarded as a filter process which furnishes signals with a better signal-to-noise ratio for the corresponding purposes and accordingly enables increased sensitivity of detection.

When a predetermined proportion (for example, 10% or 50%) of the maximum light pulse intensity is exceeded (in the rising pulse edge), this can be used, for example, as the start of a light pulse. The signal indicating the start of a light pulse can be generated with a corresponding trigger after optoelectronic conversion of the light pulse, for example.

In advantageous embodiment forms, the digital values which are stored in the shift register before the marking value and/or the digital values which are stored in the shift register after the marking value are summed, particularly before the sum is transmitted to a control computer via a data bus. To this end, an evaluation circuit can preferably comprise a readout circuit with an input for a trigger signal, at least one data input which is connected to the data output of the shift register, and at least one sum output, wherein the readout circuit reads out the register stages when the trigger signal is present and sums digital values stored before the marking value and/or sums digital values stored after the marking value and outputs them to the sum output. Summing before transmission makes it possible to reduce the required bandwidth so that a high excitation pulse frequency can be used.

For example, the input of the readout circuit can be connected to the input of the delay circuit to provide the trigger signal. Summing then starts with the next light pulse. Alternatively, the signals indicating the light pulses can be delayed separately in a circuit and then fed to the input of the readout circuit. This delay advisably takes place in such a way that the trigger signal is outputted before the next respective light pulse such that the readout process is terminated at the latest at this next light pulse.

As an alternative to summing, the register contents, i.e., raw data, can be stored and/or transmitted.

It is possible to store more than one marking value in the shift register per illumination cycle. To this end, for example, the evaluation circuit can accept a corresponding quantity of delays (explicitly for this purpose) or can determine the additional delays automatically from (exactly) one predefined delay. Then, for each of these delays, every signal indicating a light pulse is outputted by it in a delayed manner, for example, by means of a corresponding quantity of delay circuits. For example, Z marking values can be stored in the shift register by means of Z delays of this kind. Accordingly, Z+1 time windows are defined. This makes it possible, for example, to evaluate the sums of these time windows relative to one another. Independently, the evaluation circuit can accept a delay which indicates an end of the detection (before the start of the next illumination cycle).

It is advantageous when the evaluation circuit comprises at least one additional shift register and a switching circuit which alternately connects the shift registers (for a plurality of consecutive light pulses) to the analog-to-digital converter, particularly also to the delay circuit. In this way, one shift register can serve for storage, while another is read out. For example, the input of the switching circuit can be connected to the input of the delay circuit. Alternatively, the signals indicating the light pulses can be delayed separately in a circuit and then fed to the input of the switching circuit.

The invention also comprises a microscope, particularly a confocal raster scanning microscope, with a light source suitable for pulsed operation, a pulse generator for controlling the light source for emitting light pulses or a pulse monitor for monitoring the generated light pulses, an optoelectronic detector and an evaluation circuit in one of the configurations described above, wherein the input of the analog-to-digital converter is connected to the output of the detector or can be connected to the latter by means of a switch. A pulse monitor can be a photodiode, for example, to which a proportion of the emitted light intensity is directed.

The evaluation circuit preferably has a delay circuit with a predefined or predefinable delay, the signal input of the delay circuit being connected to the pulse generator or to the pulse monitor. The microscope preferably comprises operating means for setting the delay of the delay circuit, particularly a slider, particularly in a graphical user interface of a control unit as operating means. This allows the delay of the signal indicating a light pulse to be calibrated for storing the marking value so that the marking value is stored in the shift register (relative to the start time) at the end time of every exciting light pulse. This delay is characteristic of the pulsed light source so that calibration need only be carried out once for every pulsed light source. Therefore, the delay circuit can advantageously have a delay corresponding to a duration of the light pulses, which delay can be predefined at the factory, for example. The adjustment of the delay can preferably (also) be carried out by the user, who could accordingly set the suppression of excitation light depending on the application: improved signal-to-noise ratio by setting a first delay by which the delayed signal indicating the light pulse is outputted (directly) at the end of the light pulse, for a more sensitive measurement, or poorer signal-to-noise ratio by setting a first delay by which the delayed signal indicating the light pulse is outputted during the light pulse but before the end of the light pulse for a faster measurement.

For example, when the maximum light pulse intensity falls below (in the falling pulse edge) a predefined proportion (for example, 10% or 50%), this can be considered as the end of a light pulse.

In advantageous microscope configurations, the evaluation circuit comprises a readout circuit, described above, and is connected via a data bus to a control unit for transmitting the detected fluorescence events, wherein the readout circuit is arranged in front of the data bus. Summing before transmission makes it possible to reduce the required bandwidth so that a high excitation pulse frequency can be used.

Of particular advantage is a microscope, particularly a confocal raster scanning microscope, with a light source suitable for pulsed operation, a pulse generator for controlling the light source for emitting light pulses or a pulse monitor for monitoring the generated light pulses, an optoelectronic detector and a delay circuit for a signal indicating a light pulse, comprising a circuit for occasional, at least partial deactivation of the detector, particularly by controlling a voltage of the detector, particularly a dynode voltage, wherein this circuit is connected to the output of the delay circuit such that the detector is deactivated by outputting the delayed signal, particularly in such a way that the detector does not amplify light incident upon it. For example, a circuit according to US 2001/149388 A1, the disclosure of which is incorporated in its entirety herein, can be used as circuit for controlling a voltage of the detector.

Instead of, or in addition to, the temporally separate data acquisition with continuously active detector, the detector itself can be activated in this way only periodically, for example, amplification is switched on at time $t_{ON}$ after every exciting light pulse and amplification is switched off at time $t_{OFF}$ after every exciting light pulse, while, for example, the data capture passes continuously into the shift register or another storage. The advantage is that no "dazzling" and overdriving of the detector can come about in case of fluorescence detection when the detector is exposed to the light intensities during excitation which are typically high in comparison to the subsequent fluorescence. To this end, time $t_{ON}$ is so predefined that it occurs substantially at the end of the excitation pulse or coincides with it. To this end, for example, the delay circuit delays a signal indicating a light pulse by duration $\Delta t_{ON}$. A second delay circuit can delay the signal by duration $\Delta t_{OFF}$ and output it, whereupon the detector voltage is again switched in such a way that the amplification is switched off. Alternatively, this switching can take place at the occurrence of a signal indicating a light pulse (corresponding to $\Delta t_{OFF}=0$).

Instead of a shift register, a counter can be arranged and used with equivalent effect. The counter is optionally either incremented by the digital values outputted by the analog-to-digital converter starting from the output by the delay circuit of the delayed signal indicating a light pulse to a second delayed signal or to the next (not-delayed) signal indicating a light pulse in order to count fluorescence events, or is incremented by the digital values outputted by the analog-to-digital converter starting from the (not-delayed) signal indicating a light pulse to the output by the delay circuit of the delayed signal indicating a light pulse in order to count scattered light events.

It is also possible to provide two counters, one of which is incremented by the digital values outputted by the analog-to-digital converter starting from the output by the delay circuit of the delayed signal indicating a light pulse to a second delayed signal or to the next (not-delayed) signal indicating a light pulse, and the other is incremented by the digital values outputted by the analog-to-digital converter starting from the (not-delayed) signal indicating a light pulse to the output by the delay circuit of the delayed signal indicating a light pulse.

A spectral separation can be carried out in addition to the temporal separation of fluorescent light and scattered light. In particular, scattered light can be selectively spectrally blocked from the detector after a spatial-spectral splitting, for example, by means of an obstruction with a width corresponding to the line width of an excitation line and/or a Raman scattering.

BRIEF DESCRIPTION OF THE DRAWINGS

Corresponding parts are designated by the same reference numerals in all of the drawings.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
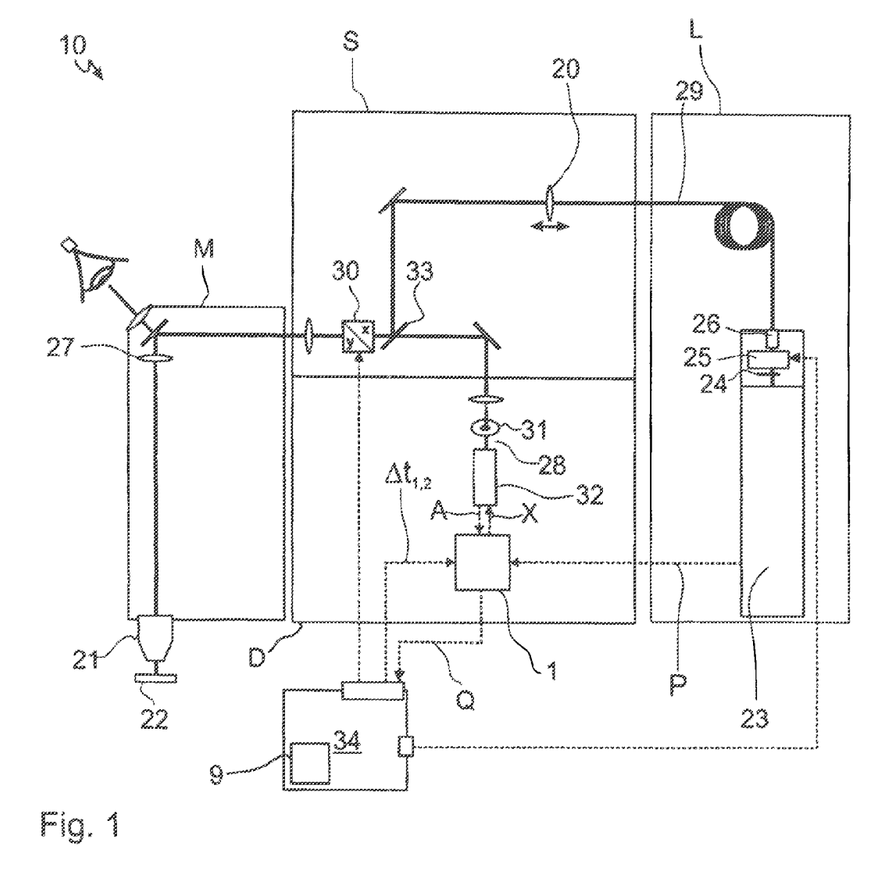
FIG. 1 shows a schematic diagram showing a microscope with an circuit.

FIG. 1 is a schematic depiction of an evaluation circuit 1 in a laser scanning microscope 10 (LSM). The LSM 10 is constructed modularly from an illumination module L with a pulsed laser as tight source 23, a scanning module S, a detection module D and microscope unit M with microscope objective 21.

Before being fed into the scanning unit S via fiber coupler 26, light-conducting fibers 29 and coupling optics 20, the light of laser 23 can be influenced by the control unit 34 through a light trap 24 and an attenuator 25, for example, an acousto-optically adjustable filter (acousto-optic tunable filter or AOTF). It passes via the main beamsplitter 33 and X-Y scanning unit 30, which has, for example, two galvanometer mirrors (not shown), through the microscope objective 21 to the sample 22, where it illuminates a focal volume (not shown). With each light pulse, the pulsed light source 23 outputs a signal P indicating the start of the light pulse, for example, by means of a trigger which is connected to a monitor diode and thus indicates the rising edge of the illumination intensity.

In other embodiment forms (not shown), coupling into light-conducting fibers, and the light-conducting fibers in particular, can be omitted.

Light scattered in the sample 22 and fluorescent light emitted by the sample 22 passes through the microscope objective 21 and then via the scanning unit 30 through the main beamsplitter 33 into the detection module D. The main beamsplitter 33 can be constructed, for example, as a dichroic color splitter in order to keep excitation light away from the detection module D as far as possible. For example, the detection module D has a detection channel with a pinhole aperture 31, a filter 28 and a detector 32, for example, a photomultiplier (PMT). The detector 32 is outfitted with art operating circuit according to US 2001/0015411 A1, for example. Instead of a pinhole aperture 31, a slit diaphragm (not shown) cart also be used in case of linear illumination, for example. The confocal pinhole aperture 31 serves to discriminate sample light that does not originate from the focal volume. Therefore, the detector 32 detects exclusively light from the focal volume. It is connected to an evaluation circuit 1. In other embodiment forms (not shown), the evaluation circuit 1 can be integrated in the detector 32; alternatively, it can be arranged outside of the detection module D.

The confocally illuminated, captured focal volume cart be moved along a raster through the sample 22 by means of the scanning unit 30 in order to capture an image pixel by pixel by rotating the galvanometer mirrors of the scanning unit 30 in a specific manner. The movement of the galvanometer mirrors, the switching of the illumination by means of the light traps 24 or attenuators 25, and the evaluation circuit 1 are controlled by the control unit 34 via one or more corresponding interfaces. In particular, the control unit 34 can specify a first delay $\Delta t_1$ and, optionally, a second delay $\Delta t_2$ for the evaluation circuit 1. The control unit can be outfitted in each instance with a slider for adjusting the delays $\Delta t_1$, $\Delta t_2$ to allow a user to set the delays $\Delta t_1$, $\Delta t_2$. Sliders of this type can be provided as operator's controls, for example, by means of a graphical user interface in a display device of the control unit 34, which can be actuated by the user by means of a mouse or by means of a touch-sensitive medium.

The evaluation circuit 1 is further connected to the light source 23 which outputs a signal P (the trigger signal) indicating the light pulse to the evaluation circuit 1 at the start of every light pulse, for example, by means of a monitor diode (not shown) which is coupled with the beam path, a trigger being arranged upstream of the monitor diode. The detector 32 outputs its intensity signal A—the analog anode signal in case of the PMT—to the evaluation circuit 1 which determines digital intensity values Q therefrom. Its operating circuit receives from the evaluation circuit 1 a switching signal X for a fast shut-down of its amplification function, for example. This operating circuit and the means for transmitting the switching signal X can be omitted in of her embodiment forms.

The data acquisition of intensity values Q by the evaluation circuit 1 of the detector 32 takes place through the control unit 34. The evaluating unit/control unit 34 can be a commercially available electronic computer, for example. The control unit 34 is connected to the evaluation circuit 1, for example, via a data bus by LVDS, for transmitting data F and $\Delta_{1(,2)}$.

Figure 2:
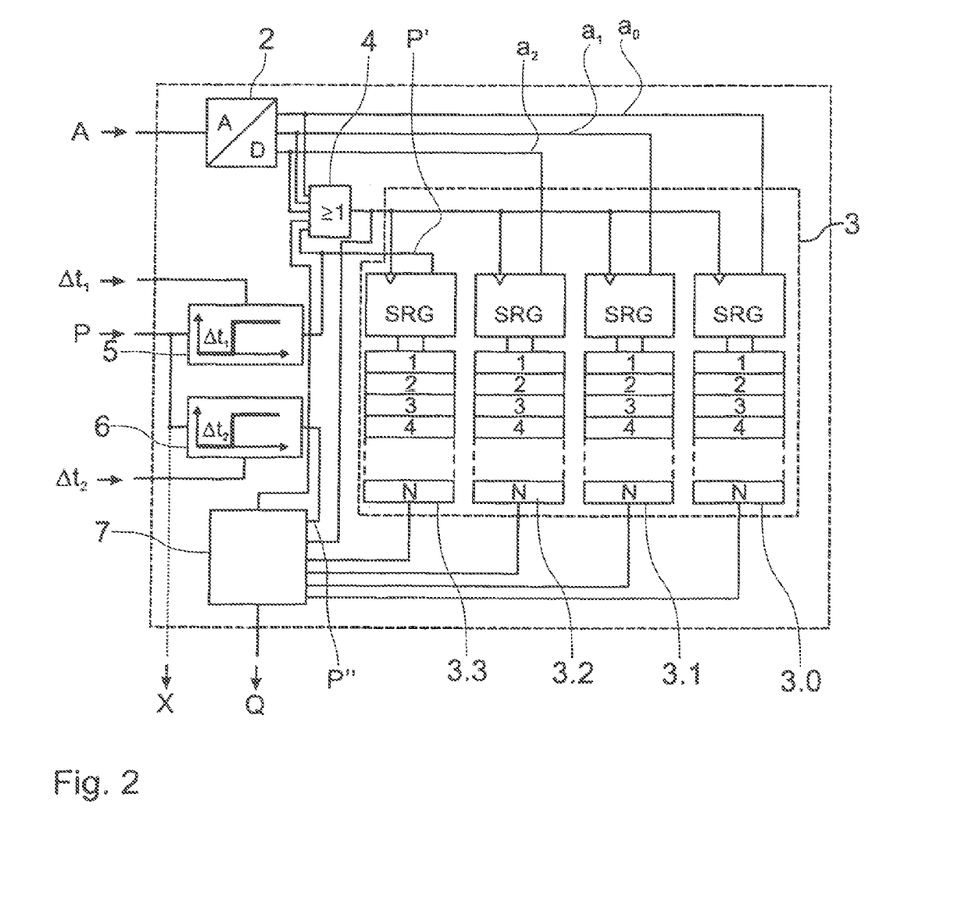
FIG. 2 shows a schematic diagram showing a first evaluation circuit with a shift register.

FIG. 2 schematically shows a first evaluation circuit 1 which can be used, for example, in microscope 10 according to FIG. 1. It can be realized by means of a field programmable gate array (FPGA). It includes an analog-to-digital converter 2, a shift register 3 (SRG), a combinational gate 4, a first delay circuit 5, a second delay circuit 6 and a readout circuit 7. The ADC 2 has, for example, three quantization levels and can therefore count a maximum of seven photons whose intensity curves overlap temporally and can output the quantity as digital value a. To this end, it is connected, for example, to a reference voltage which corresponds to an intensity signal A from seven time-coincident fluorescence events. The SRG 3 is four bits wide, i.e., one bit wider than is necessary for storing the digital values a, and N bits long, for example, N=64. Internally, it is formed of four shift registers 3.0, 3.1, 3.2 and 3.3, for example, each having a width of one bit and a length of N=64.

The evaluation circuit 1 can be formed, for example, as a plug-in module so that it can be exchanged for another evaluation circuit with little effort. To this end, plug contacts can be provided for accepting the detector signal A, the signal P indicating a start of a light pulse, delays $\Delta t_1$ and $\Delta t_2$ and for outputting intensity values Q and, optionally, switching signal X. In view of the fact that the second delay depends only on the duration of the illuminating light pulse, the first delay $\Delta t_1$ can be fixed as variable instead of acceptance.

Three bits of the data input of SRG 3 are connected to the output of the ADC 2 such that the digital value a presently outputted by the ADC 2 is present at the input stage of the SRG 3. The fourth bit of the data input of the SRG 3 is connected to the output of the first delay circuit 5 and serves for storage of a marking bit as marking value for the expiration of the adjusted first delay $\Delta t_1$ in the current illumination cycle.

The clock input of the SRG 3 is likewise connected to the output of the ADC 2 via the OR gate 4. It is also connected to the evaluation circuit 1 and to the first delay circuit 5 via the same gate 4. The OR gate 4 causes the contents of the register stages to be shifted into the next respective register stage when at least one of the inputs of the combinational gate 4 is set. For example, as soon as at least one of data bits $a_0$, $a_1$, $a_2$ is set by the conversion of the intensity signal A in the ADC 2, the digital value a consisting of these bits is stored in the SRG 3. A storage also takes place when the first delay circuit 5 outputs the delayed signal P by duration $\Delta t_1$ after the arrival of signal P indicating a light pulse. The present digital value a is then stored next to the marking bit in the SRG 3.

In alternative embodiment forms (not shown), a digital comparator can be connected between the ADC 2 and the OR gate 4 in place of the direct connection of the OR gate 4 to the output of the ABC 2, which digital comparator compares the applied digital value a with the value stored in the first register stage and sets its output exclusively when the stored value differs from the present digital value a. In this way, sequences of decreasing (non-zero) intensity values A can also be stored.

After the expiration of the second delay $\Delta t_2$, the second delay circuit 6 outputs the second delayed signal P''' and accordingly indicates the end of the recording in the present illumination cycle. Advisably, the second delay $\Delta t_2$ is predetermined in such a way that the time remaining in the second delayed signal P''' until the next signal P indicating the start of a light pulse is sufficient for reading out the shift register. Since the necessary remaining time depends only on the length of the SRG 3 and its maximum clock frequency, the second delay $\Delta t_2$ can be fixed as variable instead of acceptance by the control unit.

During each illumination cycle, the readout circuit 7 accepts the clock signal of the SRG 3 in parallel with the SRG 3 in order to count the quantity W of the filled register stages. As soon as the readout circuit 7 receives the second delayed signal P''', it shifts the shift register by the N-W unused stages and then serially reads out the last respective stage of the SRG 3 and shifts the contents of the SRG 3 by one stage by setting an input of the OR gate 4 and then resetting it again. As an alternative to the serial readout, the readout circuit 7 can also be connected to the SRG 3 such that it can read out a plurality of stages or all of the stages.

The readout circuit sums the 3-bit digital values a which are read out from the SRG 3 in a first counter until it identifies the marking bit in the fourth bit of a register stage. It then sums the rest of the 3-bit digital values a in a second counter. After the last digital value a, the counters can be read out as digital intensity values Q and then initialized. Alternatively, they are incremented over a plurality of illumination cycles before being read out. When only scatter intensities are to be measured, the counting and readout can be restricted to the first counter. Correspondingly, counting and readout can be restricted to the second counter when only fluorescence events are to be measured. The readout circuit 7 needs only one counter in embodiment forms of this type.

The signal P indicating the light pulse is passed to the detector 2 by the evaluation circuit 1, for example, without manipulation, as switching signal X, whereupon the detector 2 switches off or switches over or at least reduces one of its operating voltages. For example, the first dynode voltage, and thus protects itself from being dazzled by high light intensity. As an alternative to simply passing on the signal P indicating the light pulse as switching signal X, the evaluation circuit 1 or a separate circuit (not shown) could delay the resetting of the switching signal X, for example, by means of a sample and hold circuit.

To allow capture of Raman scattering in addition to or as alternative to fluorescence events, the detector may not be deactivated during the illuminating light pulse. Therefore, in alternative embodiment forms, the readout circuit 1 can completely suppress the switching signal X. Preferably, the evaluation circuit 1 accepts a further signal from the control unit 34, on the basis of which it determines whether switching signals X are to be generated or suppressed.

Figure 3:
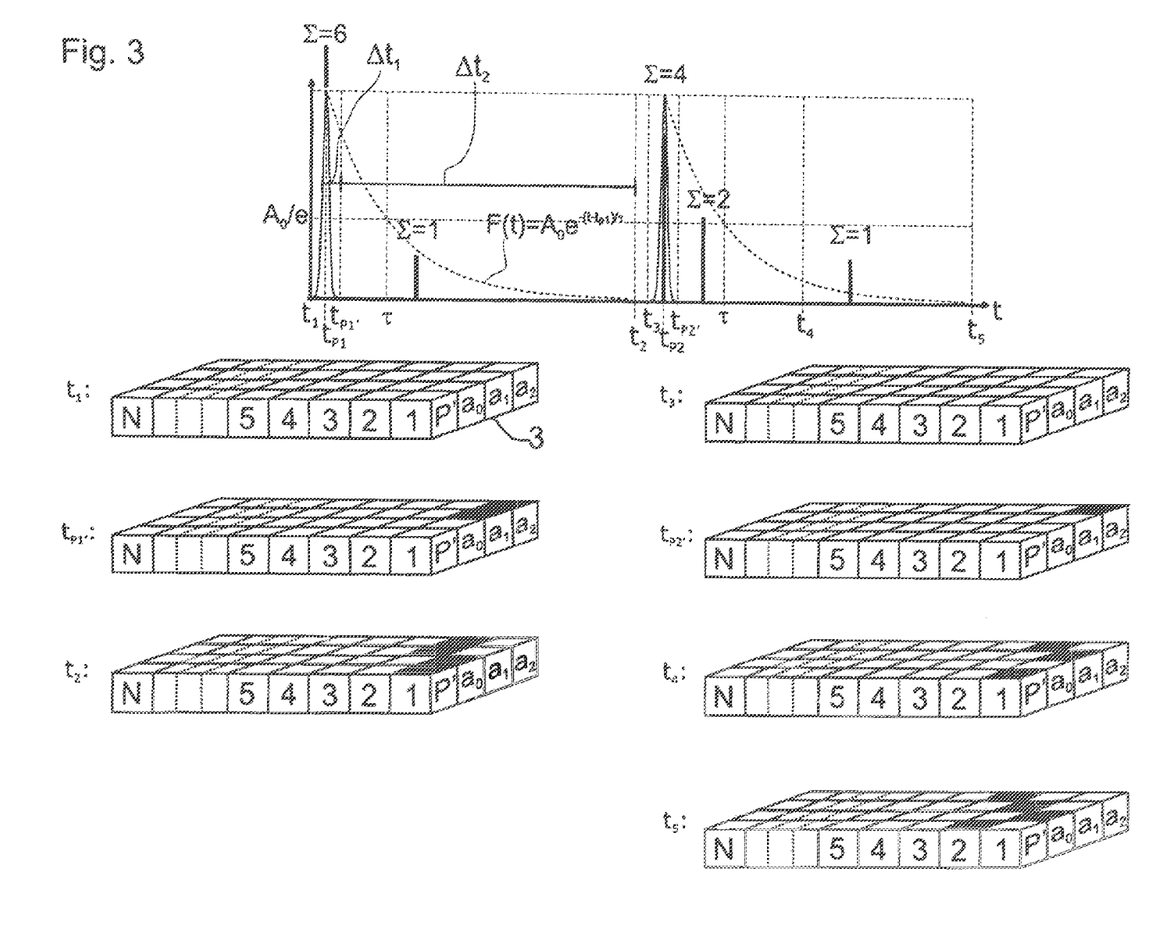
FIG. 3 shows a diagram depicting the assignment of fluorescence events to register stages in the first evaluation circuit.

FIG. 3 shows a sequence of fluorescence events and the resulting entries in the shift register 3 when an evaluating unit according to FIG. 2 is used. The shifting of the SRG 3 takes place to the left in the drawing. The curve of the illuminating light pulse is indicated next to the exponential decay curve of the fluorescence in the illumination cycles. Detected photons are indicated by lines in bold. In the first illumination cycle [$t_1$, $t_3$], for example, six scattered photons are first detected and then one individual fluorescence event is detected by the detector 2. In the second illumination cycle [$t_3$, $t_5$], four scattered photons are detected first, then two simultaneously occurring fluorescence events and later one individual fluorescence event.

The reading of the SRG 3 is shown at five different times. At the start of each illumination cycle (t1, t3, . . . ), it is empty. At the later times, the set bits are marked by black boxes. It can be seen how digital values a which are already stored are retained and shifted left when new digital values a have been determined. Since the SRG 3 is shifted only when necessary; i.e., when photons are actually detected, the marking bit for the occurrence of the delayed signal P at the end of a illumination cycle is not always in the same register stage.

Figure 4:
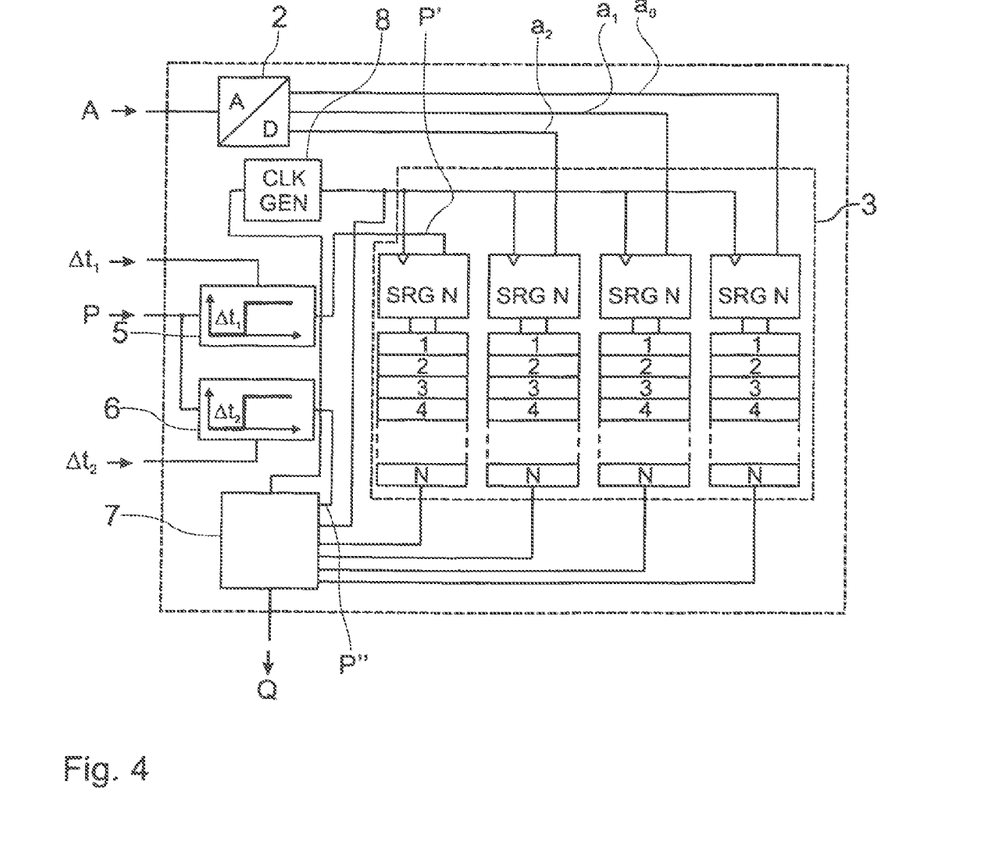
FIG. 4 shows a schematic diagram showing a second evaluation circuit with two shift registers.

FIG. 4 schematically shows a second evaluation circuit 1 which can be used, for example, in FIG. 1. In contrast to the evaluation circuit 1 shown in FIG. 2, it does not have a combinational gate but rather a clock generator 8 which applies a fixed clock to the clock input of the shift register 3 and thus continuously shifts the shift register 3. The readout circuit 7 can switch the clock generator 8 on and off, in further embodiment forms, it can also set the clock frequency, for example, according to a further signal F (not shown) to be accepted by the control unit 34.

Figure 5:
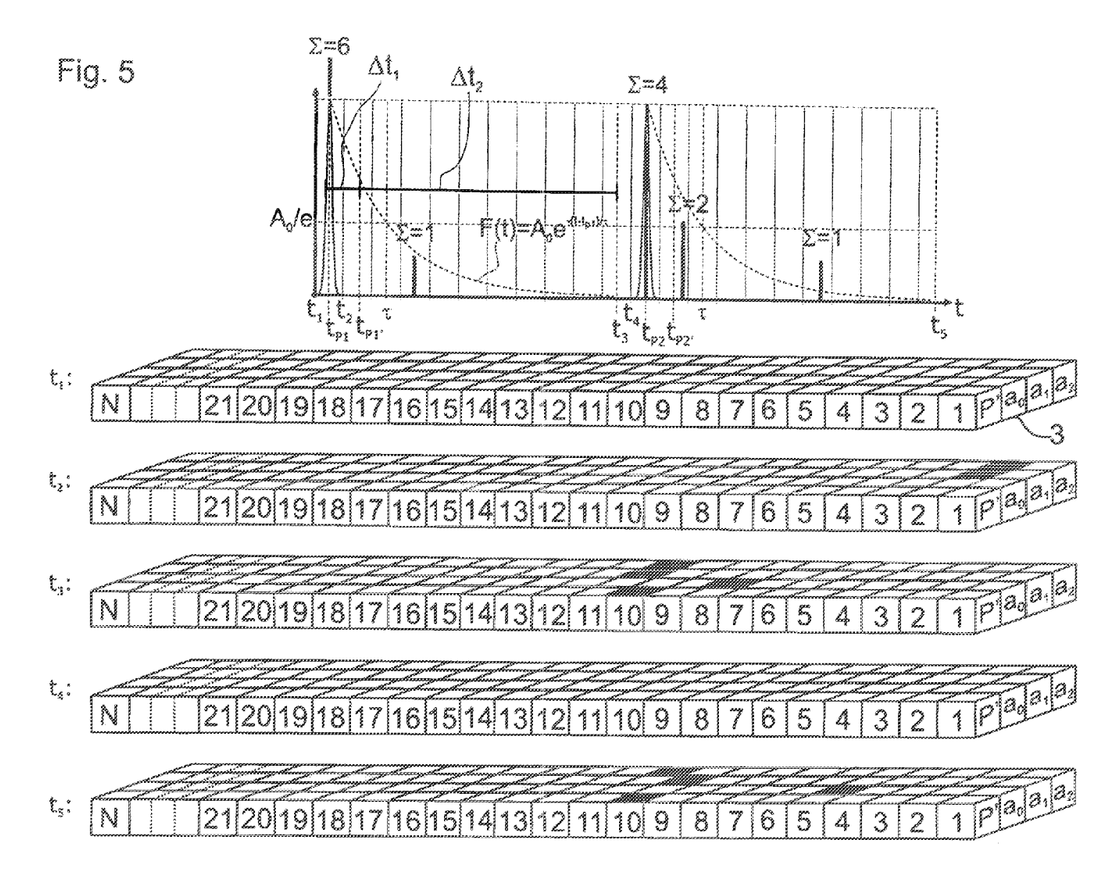
FIG. 5 shows a schematic diagram showing a third evaluation circuit with one shift register.

FIG. 5 shows a sequence of fluorescence events and the resulting entries in the shift register 3 when an evaluating unit according to FIG. 4 is used. It can be seen that the marking bit for the delayed signal P' lies in the same stage in every illumination cycle regardless of the detection of photons because of the fixed clock.

Figure 6:
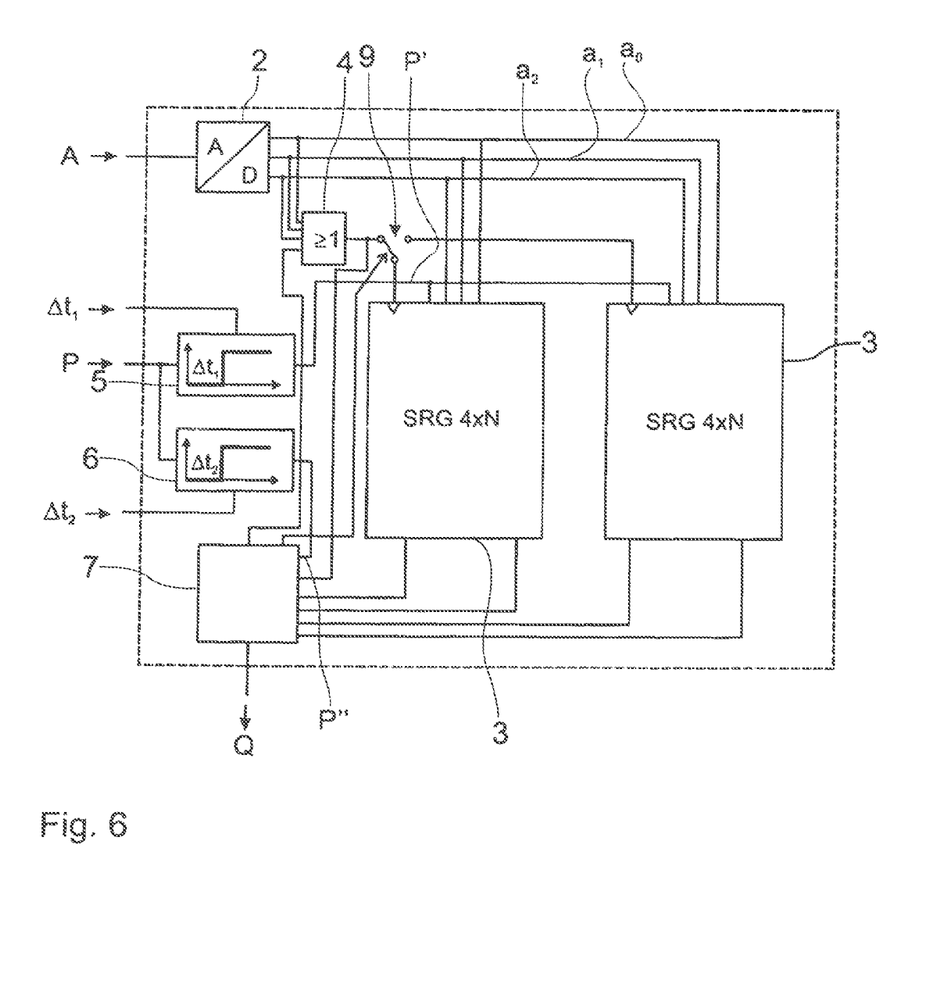
FIG. 6 shows a diagram depicting the assignment of fluorescence events to register stages in the second evaluation circuit.

FIG. 6 schematically shows a third evaluation circuit 1 which can be used in FIG. 1, for example. In addition to the evaluation circuit 1 shown in FIG. 2, it has a second shift register 3. The two shift registers 3 are alternately used for storage by switching switch 9. In case of odd-number light pulses, the fluorescence events occurring in the respective measurement interval are stored in the first shift register 3, and with even-number light pulses the fluorescence events occurring in the respective measurement interval are stored in the second shift register 3. While storage takes place in the one shift register 3, the other shift register 3 can be read out. Accordingly, the second delay circuit 6, for example, can be dispensed with when the readout circuit 7 accepts the signal P which is not delayed and switches the switch 9 as soon as such a signal P is detected. The SRG 3 which is not connected to gate 4 can then read them out serially or, alternatively, in parallel by means of a separate clock line (not shown for the same of clarity).

Two (or more) shift registers 3 can also be connected for alternately storing and reading out in an embodiment form according to FIG. 2.

In all of the embodiment forms, a simple trigger can be used instead of an analog-to-digital converter. A plurality of time-coincident fluorescence events are then counted as only one. Detected photons are lost in this way, but the shift register 3 then needs only one bit for the digital values. A further bit can be provided in addition for the marking value so that the shift register 3 only has a width of two bits, for example.

While this invention his been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

LIST OF REFERENCE NUMERALS 1 evaluation circuit
2 analog-to-digital converter
3 shift register
4 OR gate
5 first delay circuit
6 second delay circuit
7 readout circuit
8 clock generator
9 switch
10 laser scanning microscope
20 collimating optics
21 microscope objective
22 sample
23 laser
24 light trap
25 attenuator
26 fiber coupler
27 tube lens
28 filter
29 dichroic beamsplitter
30 scanning unit
31 pinhole diaphragm
32 photomultiplier
33 main beamsplitter
34 control unit
35 light source

The invention claimed is:

1. An evaluation circuit for evaluating the electric signals of an optoelectronic detector, comprising:
   an analog-to-digital converter comprising:
      an input configured to connect to an output of the detector;
      an output configured to output a digital value;
   a shift register comprising:
      at least one data input;
      a clock input;
      a plurality of register stages; and
      at least one data output;
   wherein the output of the analog-to-digital converter is connected to the data input of the shift register and also to the clock input of the shift register, so that the contents of the shift register are shifted by one stage as a result of said digital value differing from zero.

2. The evaluation circuit according to claim 1, further comprising:
   a delay circuit with variably adjustable time delay, the delay circuit comprising:
      an input configured to receive a signal indicating a light pulse; and
      an output configured to output the signal after a selected delay as a delayed signal;
   wherein the output of the delay circuit is connected to the data input of the shift register such that, by outputting the delayed signal, a marking value is presented at the data input in addition to or instead of the digital value.

3. The evaluation circuit according to claim 2, further comprising:
   a readout circuit comprising:
      an input configured to receive a trigger signal;
      at least one data input which is connected to the data output of the shift register; and
      at least one sum output;
   wherein the readout circuit is configured to read out the register stages when the trigger signal is present;
   wherein the readout circuit is also configured to:
      sum digital values stored before the marking value; and/or
      sum digital values stored after the marking value; and
   wherein the readout circuit is further configured to output the summed values to the sum output.

4. The evaluation circuit according to claim 1, further comprising:
   at least one additional shift register; and
   a switching circuit which, for a plurality of consecutive light pulses, is configured to alternately connect the shift registers to the analog-to-digital converter.

5. A microscope comprising:
   a light source configured for pulsed operation;
   at least one of:
      a pulse generator configured to control the light source to emit light pulses; and
      a pulse monitor configured to monitor the generated light pulses;
   an optoelectronic detector; and
   the evaluation circuit according to claim 1;
   wherein the input of the analog-to-digital converter is connected to the output of the detector or is configured to be connected to the output of the detector by means of a switch.

6. The microscope according to claim 5;
   wherein the evaluation circuit comprises:
      a delay circuit with variably adjustable time delay, the delay circuit comprising:
         an input configured to receive a signal indicating a light pulse; and
         an output configured to output the signal after a presently selected delay as a delayed signal;
      wherein the output of the delay circuit is connected to the data input of the shift register such that, by outputting the delayed signal, a marking value is presented at the data input in addition to or instead of the digital value; and
      wherein the signal input of the delay circuit is connected to the pulse generator or to the pulse monitor.

7. The microscope according to claim 6;
   wherein the delay circuit has a delay corresponding to a duration of the light pulses.

8. The microscope according to claim 6, further comprising:
operating means for setting the delay of the delay circuit.

9. The microscope according to claim 6;
wherein the evaluation circuit comprises:
  a readout circuit comprising:
    an input configured to receive a trigger signal;
    at least one data input which is connected to the data output of the shift register; and
    at least one sum output;
  wherein the readout circuit is configured to read out the register stages when the trigger signal is present;
  wherein the readout circuit is also configured to:
    sum digital values stored before the marking value; and/or
    sum digital values stored after the marking value; and
  wherein the readout circuit is further configured to output the summed values to the sum output;
wherein the evaluation circuit is connected via a data bus to a control unit configured to transmit detected fluorescence events; and
wherein the readout circuit is arranged in front of the data bus.

10. A microscope comprising:
a light source configured for pulsed operation;
the evaluation circuit according to claim 1;
at least one of:
  a pulse generator configured to control the light source to emit light pulses; and
  a pulse monitor configured to monitor the emitted light pulses;
an optoelectronic detector; and
a delay circuit with variably adjustable time delay, the delay circuit comprising:
  an input configured to receive a signal indicating a light pulse; and
  an output configured to output the signal after a presently selected delay as a delayed signal;
a deactivation circuit configured to occasionally, at least partially, deactivate the optoelectronic detector;
wherein the deactivation circuit is connected to the output of the delay circuit such that the optoelectronic detector is deactivated by outputting the delayed signal.

11. A method for recording fluorescence events by means of an optoelectronic detector, comprising:
radiating light pulses onto a sample by means of a light source;
capturing light from the sample by means of the optoelectronic detector;
converting the captured light into an electric signal and
feeding the electric signal to an analog-to-digital converter to generate a digital value;
outputting the digital value from the analog-to-digital converter; and
storing the outputted digital value in an input stage of a shift register;
wherein the method farther comprises at least one further step selected from the group consisting of:
  summing digital values which are stored in the shift register before a marking value; and
  summing digital values which are stored in the shift register after a marking value.

12. The method according to claim 11;
wherein contents of the shift register are shifted by one stage at the occurrence of a non-zero digital value.

13. The method according to claim 11;
wherein the contents of the shift register are shifted by one stage repeatedly after a predefined time, where the predefined time is provided by a clock generator having a predefined or predefinable clock frequency.

* * * * *